(12) United States Patent  
Fu et al.

(10) Patent No.: US 12,673,051 B2  
(45) Date of Patent: \*Jul. 7, 2026

(54) COMPOSITION AND PRODUCT THEREOF

(71) Applicants: SHENZHEN FIRST UNION TECHNOLOGY CO., LTD., Shenzhen City (CN); SHENZHEN HERUI BIOTECHNOLOGY CO., LTD., Shenzhen City (CN)

(72) Inventors: Guofeng Fu, Shenzhen City (CN); Xing Zhou, Shenzhen City (CN); Wenwen Huang, Shenzhen City (CN); Zhongli Xu, Shenzhen City (CN); Yonghai Li, Shenzhen City (CN)

(73) Assignees: SHENZHEN FIRST UNION TECHNOLOGY CO., LTD., Shenzhen City (CN); SHENZHEN HERUI BIOTECHNOLOGY CO., LTD., Shenzhen City (CN)

( \* ) Notice: Subject to any disclaimer, the term of this patent is extended or adjusted under 35 U.S.C. 154(b) by 312 days.

This patent is subject to a terminal disclaimer.

(21) Appl. No.: 17/915,050

(22) PCT Filed: Mar. 26, 2021

(86) PCT No.: PCT/CN2021/083346  
§ 371 (c)(1),  
(2) Date: Sep. 27, 2022

(87) PCT Pub. No.: WO2021/190642  
PCT Pub. Date: Sep. 30, 2021

(65) Prior Publication Data  
US 2023/0106237 A1 Apr. 6, 2023

(30) Foreign Application Priority Data

Mar. 27, 2020 (CN) .......................... 202010227895.8  
Jun. 24, 2020 (CN) .......................... 202010589322.X

(51) Int. Cl.  
A61K 31/455 (2006.01)  
A23G 4/06 (2006.01)  
A24D 3/06 (2006.01)

(52) U.S. Cl.  
CPC .............. *A61K 31/455* (2013.01); *A23G 4/06* (2013.01); *A24D 3/06* (2013.01)

(58) Field of Classification Search  
CPC .......... A61K 31/455; A23G 4/06; A24D 3/06  
See application file for complete search history.

(56) References Cited

U.S. PATENT DOCUMENTS

| | | | | |
|---|---|---|---|---|
| 4,064,253 A | * | 12/1977 | Khoe ................... | A61K 31/455 |
| | | | | 514/356 |
| 2010/0189818 A1 | * | 7/2010 | Tsai ....................... | A61K 36/16 |
| | | | | 514/474 |
| 2011/0139166 A1 | | 6/2011 | Luzenberg, Jr. | |

FOREIGN PATENT DOCUMENTS

| | | | | |
|---|---|---|---|---|
| CN | 1186614 | A | | 7/1998 |
| CN | 1651432 | A | | 8/2005 |
| CN | 101624368 | A | * | 1/2010 |
| CN | 101912496 | A | | 12/2010 |
| CN | 103461641 | A | | 12/2013 |
| CN | 103504431 | A | | 1/2014 |
| CN | 105028885 | A | | 11/2015 |
| CN | 106720890 | A | | 5/2017 |
| CN | 110150760 | A | | 8/2019 |
| CN | 110771946 | A | * | 2/2020 |
| JP | S50-94132 | | | 7/1975 |
| JP | H11-192069 | A | | 7/1999 |
| JP | 2023-519006 | A | | 5/2023 |
| WO | 2018/207888 | A1 | | 11/2018 |
| WO | 2019/082081 | A1 | | 5/2019 |

OTHER PUBLICATIONS https://en.wikipedia.org/wiki/Areca_nut (archived 2009) (Year: 2009).*

* cited by examiner

*Primary Examiner* — Blessing M Fubara  
(74) *Attorney, Agent, or Firm* — Scully, Scott, Murphy & Presser, P.C.

(57) ABSTRACT

This application provides a composition and a product thereof. The composition includes arecoline and an acid. The composition is convenient to use and widely used, with a low pH value and weak irritation.

12 Claims, No Drawings

COMPOSITION AND PRODUCT THEREOF

CROSS-REFERENCE TO RELATED APPLICATIONS

This application is a 35 U.S.C. § 371 National Phase conversion of International (PCT) Patent Application No. PCT/CN2021/083346, filed on Mar. 26, 2021, which claims the priority to Chinese Patent Application No. 202010227895.8 filed with China National Intellectual Property Administration on Mar. 27, 2020 and entitled "AEROSOL GENERATION SUBSTRATE", and Chinese Patent Application No. 202010589322.X filed with China National Intellectual Property Administration on Jun. 24, 2020 and entitled "COMPOSITION AND PRODUCT THEREOF", the contents of which are incorporated herein by reference in their entireties. The PCT International Patent Application was filed and published in Chinese.

TECHNICAL FIELD

Embodiments of this application relate to the field of chemical synthesis technologies, and particularly relate to a composition and a product thereof.

BACKGROUND

Arecoline, with a chemical name of "1,2,5,6-tetrahydro-1-methyl-3-pyridinecarboxylic acid methyl ester", is an oily liquid with a cholinergic effect. Arecoline is a compound with great application value, and preparation methods and applications thereof have always attracted attention of people.

SUMMARY

According to a first aspect, an embodiment of this application provides a composition including arecoline and an acid.

In some embodiments, the acid is selected from the group consisting of at least one of:

formic acid, acetic acid, propionic acid, butyric acid, isovaleric acid, 2-methylbutyric acid, valeric acid, 3-methylvaleric acid, 2-methyl-2-pentenoic acid, trans-2-hexenoic acid, hexanoic acid, heptanoic acid, octanoic acid, 2-nonenoic acid, decanoic acid, dodecanoic acid, tetradecanoic acid, hexadecanoic acid, octadecanoic acid, arachidic acid, benzoic acid, salicylic acid, oxalic acid, citric acid, sorbic acid, tartaric acid, adipic acid, hydrochloric acid, hydrobromic acid, glycine, alanine, valine, leucine, isoleucine, methionine, phenylalanine, proline, tryptophan, serine, tyrosine, cysteine, methionine, asparagine, glutamine, threonine, aspartic acid, glutamic acid, lysine, arginine or histidine.

In some embodiments, the arecoline and the acid have a molar ratio of n; n has a value of $0<n\leq10$, preferably $0<n\leq8$, further preferably $0<n\leq6$, further preferably $0<n\leq5$, further preferably $0<n\leq3$, and further preferably $0<n\leq2$.

In some embodiments, the arecoline and the acid form an arecoline salt.

According to a second aspect, an embodiment of this application provides a product with an areca nut flavor, where the product includes the composition according to the first aspect.

In some embodiments, the product is an aerosol generation substrate configured to be atomized to generate a smokable aerosol.

In some embodiments, the aerosol generation substrate is a liquid phase configured to be atomized by any one of a heating atomizer, an ultrasonic atomizer, an air compression atomizer or a press-type spraying apparatus to generate an aerosol.

In some embodiments, the aerosol generation substrate is a solid phase configured to generate a smokable aerosol when heated below an ignition point.

In some embodiments, the product is a filter capsule used in an aerosol-generating article.

In some embodiments, the product is a chewing gum.

DESCRIPTION OF EMBODIMENTS

This application will be further described with reference to the following embodiments.

Implementation 1

Implementation 1 of this application provides a composition including arecoline and an acid.

In some embodiments, the acid is selected from the group consisting of at least one of:

formic acid, acetic acid, propionic acid, butyric acid, isovaleric acid, 2-methylbutyric acid, valeric acid, 3-methylvaleric acid, 2-methyl-2-pentenoic acid, trans-2-hexenoic acid, hexanoic acid, heptanoic acid, octanoic acid, 2-nonenoic acid, decanoic acid, dodecanoic acid, tetradecanoic acid, hexadecanoic acid, octadecanoic acid, arachidic acid, benzoic acid, salicylic acid, oxalic acid, citric acid, sorbic acid, tartaric acid, adipic acid, hydrochloric acid, hydrobromic acid, glycine, alanine, valine, leucine, isoleucine, methionine, phenylalanine, proline, tryptophan, serine, tyrosine, cysteine, methionine, asparagine, glutamine, threonine, aspartic acid, glutamic acid, lysine, arginine or histidine.

In some embodiments, the arecoline and the acid have a molar ratio of n; n has a value of $0<n\leq10$, preferably $0<n\leq8$, further preferably $0<n\leq6$, further preferably $0<n\leq5$, further preferably $0<n\leq3$, and further preferably $0<n\leq2$.

In some embodiments, the arecoline and the acid form an arecoline salt.

In this embodiment, the arecoline and the acid are stabilized in the composition in the form of the arecoline salt. The composition includes one or more of arecoline, an acid, a solvent and an arecoline salt.

During preparation, the arecoline and the acid at different molar ratios are weighed, mixed and stirred to obtain the composition.

The prepared composition is convenient to use and widely used, with a low pH value and weak irritation.

Implementation 2

Implementation 2 of this application provides an application of the composition according to Implementation 1 in preparing an aerosol generation substrate.

In some embodiments, when the aerosol generation substrate is prepared, the arecoline has a mass percentage of 0.01-10%, preferably 0.2-10%, further preferably 1-10%, further preferably 1-5%, further preferably 1-4%, further preferably 1-3%, and further preferably 1-2%, based on total mass of the aerosol generation substrate.

In some embodiments, when the aerosol generation substrate is prepared, the acid has a mass percentage of 0.01-10%, preferably 0.2-10%, further preferably 1-10%, further preferably 1-5%, further preferably 1-4%, further preferably 1-3%, and further preferably 1-2%, based on total mass of the aerosol generation substrate.

In some embodiments, when the aerosol generation substrate is prepared, objects added to the composition include a solvent.

In some embodiments, the solvent is selected from the group consisting of at least one of:

1,2-propanediol, 1,3-propanediol, glycerol, polyethylene glycol 200, polyethylene glycol 400, dipropylene glycol ether, ethanol, water, triethyl citrate, triacetin, caprylic capric triglyceride, isopropyl alcohol, sweet orange oil, lemon oil, peppermint oil, palm oil, peanut oil, corn oil or salad oil.

In some embodiments, the solvent includes glycerol, and the glycerol has a mass percentage of 0-90%.

In some embodiments, the solvent includes propylene glycol, and the propylene glycol has a mass percentage of 9-99.8%.

In some embodiments, when the aerosol generation substrate is prepared, objects added to the composition further include a cooling agent.

In some embodiments, the cooling agent is selected from the group consisting of at least one of:

N-ethyl-2-isopropyl-5-methylcyclohexane carboxamide, N,2,3-trimethyl-2-isopropylbutamide or n-[(ethoxycarbonyl)methyl)-p-menthane-3-carboxamide.

In some embodiments, objects added to the composition further include a flavoring agent.

In some embodiments, the flavoring agent is selected from the group consisting of at least one of:

nerol, trans-2-hexenol, linalool, benzyl alcohol, 1-hexanol, leaf alcohol, alpha-terpineol, citronellol, beta-phenylethanol, linalool oxide, geraniol, isoamyl alcohol, octanol, hexanol, decanol, cinnamyl alcohol, heptanol, eugenol, maltol, ethyl maltol, thymol, isoeugenol, 2-methylbutyric acid, malic acid, n-valeric acid, n-hexanoic acid, edible acetic acid, n-caprylic acid, strawberry acid, butyric acid, citric acid, propionic acid, 3-methylvaleric acid, isovaleric acid, isoamyl acetate, amyl formate, geranyl formate, butyl formate, benzyl formate, formicacidhexenester, gamma-decanolactone, delta-nonalactone, gamma-octalactone, gamma-heptalactone, gamma-Undecalactone, delta-dodecalactone, benzaldehyde, strawberry aldehyde, cinnamaldehyde, furfural, citral, acetaldehyde, 3-methylthiopropanal, natural 3-mercapto-2-methylpentanal, isobutyraldehyde, trans-2-octenal, trans-2-nonenal, trans-2-decenal, trans, trans-2,4-heptadienal, 2,5-dimethylpyrazine, 2-acetylfuran, 2-ethyl-3 (5 or 6)-dimethylpyrazine, 2,3,5,6-tetramethylpyrazine, 2,3,5-trimethylpyrazine, 2-acetylpyrazine, acetophenone, beta-ionone, damascenone No. 2 (Firmenich), butanedione, alpha-ionone, acetoin (acetyl methyl carbinol), methyl heptenone, vanillin, ethyl vanillin, dihydrocoumarin, raspberry ketone, anisole, cedrol methyl ether, methyl-2-methyl-3-furyl disulfide, wintergreen oil, clove bud oil, 10-fold orange oil, Bois de rose oil, geranium oil, benzaldehyde, basil oil, ethyl vanillin, dihydrocoumarin, raspberry ketone, vanitrope, Tolu concrete, Peru concrete, oak extract, supercritical extract from espresso (water soluble), cocoa extract, coffee tincture, pandan leaf extract, vanilla extract, Labdanum concrete, orris oil or concrete, jasmine concrete, tree moss concrete (amber), tamarind extract, Zimbabwean tobacco extract, tobacco essence, burley tobacco extract, flue-cured tobacco absolute A, top note extract of flue-cured tobacco or top note extract of sun-cured tobacco.

It should be noted that the flavoring agent is not limited to the substances listed above, and any flavoring agent conforming to FEMA codes or CAS codes is applicable.

In some embodiments, objects added to the composition do not include nicotine and/or nicotine salts.

Implementation 3

Implementation 3 of this application provides an aerosol generation substrate including the composition and the solvent according to Implementation 1.

In some embodiments, the arecoline has a mass percentage of 0.01-10%, preferably 0.2-10%, further preferably 1-10%, further preferably 1-5%, further preferably 1-4%, further preferably 1-3%, and further preferably 1-2%, based on total mass of the aerosol generation substrate.

In some embodiments, the acid has a mass percentage of 0.01-10%, preferably 0.2-10%, further preferably 1-10%, further preferably 1-5%, further preferably 1-4%, further preferably 1-3%, and further preferably 1-2%.

In some embodiments, the solvent is selected from the group consisting of at least one of:

1,2-propanediol, 1,3-propanediol, glycerol, polyethylene glycol 200, polyethylene glycol 400, dipropylene glycol ether, ethanol, water, triethyl citrate, triacetin, caprylic capric triglyceride, isopropyl alcohol, sweet orange oil, lemon oil, peppermint oil, palm oil, peanut oil, corn oil or salad oil.

In some embodiments, the solvent includes glycerol, and the glycerol in the aerosol generation substrate has a mass percentage of 0-90%.

In some embodiments, the solvent includes propylene glycol, and the propylene glycol in the aerosol generation substrate has a mass percentage of 9-99.8%.

In some embodiments, the aerosol generation substrate further includes a cooling agent.

In some embodiments, the cooling agent is selected from the group consisting of at least one of:

N-ethyl-2-isopropyl-5-methylcyclohexane carboxamide, N,2,3-trimethyl-2-isopropylbutamide or n-[(ethoxycarbonyl)methyl)-p-menthane-3-carboxamide.

In some embodiments, the aerosol generation substrate further includes a flavoring agent.

In some embodiments, the flavoring agent is selected from the group consisting of at least one of:

nerol, trans-2-hexenol, linalool, benzyl alcohol, 1-hexanol, leaf alcohol, alpha-terpineol, citronellol, beta-phenylethanol, linalool oxide, geraniol, isoamyl alcohol, octanol, hexanol, decanol, cinnamyl alcohol, heptanol, eugenol, maltol, ethyl maltol, thymol, isoeugenol, 2-methylbutyric acid, malic acid, n-valeric acid, n-hexanoic acid, edible acetic acid, n-caprylic acid, strawberry acid, butyric acid, citric acid, propionic acid, 3-methylvaleric acid, isovaleric acid, isoamyl acetate, amyl formate, geranyl formate, butyl formate, benzyl formate, formicacidhexenester, gamma-decanolactone, delta-nonalactone, gamma-octalactone, gamma-heptalactone, gamma-Undecalactone, delta-dodecalactone, benzaldehyde, strawberry aldehyde, cinnamaldehyde, furfural, citral, acetaldehyde, 3-methylthiopropanal, natural 3-mercapto-2-methylpentanal, isobutyraldehyde, trans-2-octenal, trans-2-nonenal, trans-2-decenal, trans,trans-2,4-heptadienal, 2,5-dimethylpyrazine, 2-acetylfuran, 2-ethyl-3 (5 or 6)-dimethylpyrazine, 2,3,5,6-tetramethylpyrazine, 2,3,5-trimethylpyrazine, 2-acetylpyrazine, acetophenone, beta-ionone, damascenone No. 2 (Firmenich), butanedione, alpha-ionone, acetoin (acetyl methyl carbinol), methyl heptenone, vanillin, ethyl vanillin, dihydrocoumarin, raspberry ketone, anisole, cedrol methyl ether, methyl-2-methyl-3-furyl disulfide, wintergreen oil, clove bud oil, 10-fold orange oil, Bois de rose oil, geranium oil, benzaldehyde, basil oil, ethyl vanillin, dihydrocoumarin, raspberry ketone, vanitrope, Tolu concrete, Peru concrete, oak extract, supercritical extract from espresso (water soluble), cocoa extract, coffee tincture, pandan leaf extract, vanilla extract, Labdanum concrete, orris oil or concrete, jasmine concrete, tree moss concrete (amber), tamarind extract, Zimbabwean tobacco extract, tobacco essence, burley tobacco extract, flue-cured tobacco absolute A, top note extract of flue-cured tobacco or top note extract of sun-cured tobacco.

It should be noted that the flavoring agent is not limited to the substances listed above, and any flavoring agent conforming to FEMA codes or CAS codes is applicable.

In some embodiments, the aerosol generation substrate does not include nicotine and/or nicotine salts.

Embodiment 1

An aerosol generation substrate is prepared according to the following formula:

566.6 g of propylene glycol, 400 g of glycerol, 16.7 g of benzoic acid and 16.7 g of arecoline.

Preparation method: benzoic acid and arecoline of the above formula weight are weighed and added to propylene glycol under stirring, then a formula amount of glycerol is added before stirring and filtering for bottling.

Embodiment 2

An aerosol generation substrate is prepared according to the following formula:

569.8 g of propylene glycol, 400 g of glycerol, 13.5 g of benzoic acid and 16.7 g of arecoline.

Preparation method: benzoic acid and arecoline of the above formula weight are weighed and added to propylene glycol under stirring, then a formula amount of glycerol is added before stirring and filtering for bottling.

Embodiment 3

An aerosol generation substrate is prepared according to the following formula:

570.8 g of propylene glycol, 400 g of glycerol, 12.5 g of benzoic acid and 16.7 g of arecoline.

Preparation method: benzoic acid and arecoline of the above formula weight are weighed and added to propylene glycol under stirring, then a formula amount of glycerol is added before stirring and filtering for bottling.

Comparative Example 1

An aerosol generation substrate is prepared according to the following formula:

583.3 g of propylene glycol, 400 g of glycerol and 16.7 g of arecoline.

Preparation method: arecoline of the above formula weight is weighed and added to propylene glycol under stirring, then a formula amount of glycerol is added before stirring and filtering for bottling.

The aerosol generation substrates prepared in Embodiments 1 to 3 and Comparative Example 1 are tested for pH values, and smoked by multiple subjects for evaluation of irritation based on the following evaluation criteria: 10 scores in total, 1-5 scores for weak irritation, 6-7 scores for moderate irritation, and 8-10 scores for intense irritation; the scores are mean values.

Test Results are Shown in the Following Table

| No. | Formula | pH value | Irritation score |
| --- | --- | --- | --- |
| Embodiment 1 | 566.6 g of propylene glycol, 400 g of glycerol, 16.7 g of benzoic acid and 16.7 g of arecoline | 6.1 | 4 |
| Embodiment 2 | 569.8 g of propylene glycol, 400 g of glycerol, 13.5 g of benzoic acid and 16.7 g of arecoline | 6.5 | 5 |
| Embodiment 3 | 570.8 g of propylene glycol, 400 g of glycerol, 12.5 of benzoic acid and 16.7 g of arecoline | 6.7 | 6 |
| Comparative Example 1 | 583.3 g of propylene glycol, 400 g of glycerol and 16.7 g of arecoline | 9.4 | 9 |

It can be seen from the test results that the aerosol generation substrate with benzoic acid has a pH value lower than the aerosol generation substrate prepared in Comparative Example 1.

In addition, after the aerosol generation substrate is atomized into an aerosol, smokers can take in arecoline, which is less irritating and can produce a similar effect of chewing areca.

Implementation 4

Implementation 4 of this application provides an aerosol generating system including an atomizer and the aerosol generation substrate according to implementation 3; the atomizer is configured to atomize the aerosol generation substrate to form an aerosol.

In some embodiments, the atomizer is a heating atomizer.

In some embodiments, the atomizer is an ultrasonic atomizer.

In some embodiments, the aerosol generation substrate includes arecoline, benzoic acid, glycerol and propylene glycol.

In some embodiments, the aerosol generation substrate includes arecoline, benzoic acid, glycerol and water.

In some embodiments, the aerosol generation substrate includes arecoline, benzoic acid and palm oil.

In some embodiments, the ultrasonic atomizer has an oscillation frequency greater than 1 MHz.

In some embodiments, the atomizer is an air compression atomizer or a press-type spraying apparatus.

In some embodiments, the aerosol generation substrate includes arecoline, benzoic acid and water.

In some embodiments, the aerosol generation substrate includes arecoline, benzoic acid, glycerol and water.

In some embodiments, the aerosol generation substrate includes arecoline, benzoic acid and palm oil.

Implementation 5

Implementation 5 of this application provides an application of the composition according to Implementation 1 in manufacturing an aerosol-generating article.

The aerosol-generating article is configured to be heated to generate a smokable aerosol.

In some embodiments, when the aerosol-generating article is manufactured, the arecoline has a mass percentage of 0.01-10%, preferably 0.2-10%, further preferably 1-10%, further preferably 1-5%, further preferably 1-4%, further preferably 1-3%, and further preferably 1-2%, based on total mass of raw materials of the aerosol-generating article.

In some embodiments, when the aerosol-generating article is manufactured, the acid has a mass percentage of 0.01-10%, preferably 0.2-10%, further preferably 1-10%, further preferably 1-5%, further preferably 1-4%, further preferably 1-3%, and further preferably 1-2%, based on total mass of raw materials of the aerosol-generating article.

In some embodiments, when the aerosol-generating article is manufactured, objects added to the composition include an atomization agent, an adhesive and a plant fiber.

In some embodiments, the atomization agent is selected from the group consisting of at least one of:

1,2-propanediol, 1,3-propanediol, glycerol, polyethylene glycol 200, polyethylene glycol 400, dipropylene glycol ether, ethanol, water, triethyl citrate, triacetin, caprylic capric triglyceride, isopropyl alcohol, sweet orange oil, lemon oil, peppermint oil, palm oil, peanut oil, corn oil or salad oil.

In some embodiments, when the aerosol-generating article is manufactured, the atomization agent has a mass percentage of 5-30%, preferably 10-30%, further preferably 10-25%, and further preferably 15-25%, based on total mass of raw materials of the aerosol-generating article.

In some embodiments, the adhesive is selected from the group consisting of at least one of:

carboxymethyl cellulose, hydroxypropyl methyl cellulose, polyvinyl alcohol, rosin, xanthan gum, Arabic gum, guar gum, chitosan, pectin, locust bean gum, starch, sodium alginate or shellac.

In some embodiments, when the aerosol-generating article is manufactured, the adhesive has a mass percentage of 1-20%, preferably 1-15%, further preferably 1-10%, further preferably 3-10%, and further preferably 5-10%, based on total mass of raw materials of the aerosol-generating article.

In some embodiments, the plant fiber is selected from the group consisting of at least one of:

areca nut fiber, wood pulp fiber, hemp pulp fiber, cotton pulp fiber, bagasse pulp fiber, bamboo pulp fiber or coconut pulp fiber.

In some embodiments, when the aerosol-generating article is manufactured, the plant fiber has a mass percentage of 40-80%, preferably 40-70%, further preferably 50-70%, further preferably 50-65%, and further preferably 50-60%, based on total mass of raw materials of the aerosol-generating article.

In some embodiments, objects added to the composition further include a flavoring agent.

In some embodiments, the flavoring agent is selected from the group consisting of at least one of:

nerol, trans-2-hexenol, linalool, benzyl alcohol, 1-hexanol, leaf alcohol, alpha-terpineol, citronellol, beta-phenylethanol, linalool oxide, geraniol, isoamyl alcohol, octanol, hexanol, decanol, cinnamyl alcohol, heptanol, eugenol, maltol, ethyl maltol, thymol, isoeugenol, 2-methylbutyric acid, malic acid, n-valeric acid, n-hexanoic acid, edible acetic acid, n-caprylic acid, strawberry acid, butyric acid, citric acid, propionic acid, 3-methylvaleric acid, isovaleric acid, isoamyl acetate, amyl formate, geranyl formate, butyl formate, benzyl formate, formicacidhexenester, gamma-decanolactone, delta-nonalactone, gamma-octalactone, gamma-heptalactone, gamma-Undecalactone, delta-dodecalactone, benzaldehyde, strawberry aldehyde, cinnamaldehyde, furfural, citral, acetaldehyde, 3-methylthiopropanal, natural 3-mercapto-2-methylpentanal, isobutyraldehyde, trans-2-octenal, trans-2-nonenal, trans-2-decenal, trans,trans-2,4-heptadienal, 2,5-dimethylpyrazine, 2-acetylfuran, 2-ethyl-3 (5 or 6)-dimethylpyrazine, 2,3,5,6-tetramethylpyrazine, 2,3,5-trimethylpyrazine, 2-acetylpyrazine, acetophenone, beta-ionone, damascenone No. 2 (Firmenich), butanedione, alpha-ionone, acetoin (acetyl methyl carbinol), methyl heptenone, vanillin, ethyl vanillin, dihydrocoumarin, raspberry ketone, anisole, cedrol methyl ether, methyl-2-methyl-3-furyl disulfide, wintergreen oil, clove bud oil, 10-fold orange oil, Bois de rose oil, geranium oil, benzaldehyde, basil oil, ethyl vanillin, dihydrocoumarin, raspberry ketone, vanitrope, Tolu concrete, Peru concrete, oak extract, supercritical extract from espresso (water soluble), cocoa extract, coffee tincture, pandan leaf extract, vanilla extract, Labdanum concrete, orris oil or concrete, jasmine concrete, tree moss concrete (amber), tamarind extract, Zimbabwean tobacco extract, tobacco essence, burley tobacco extract, flue-cured tobacco absolute A, top note extract of flue-cured tobacco or top note extract of sun-cured tobacco.

It should be noted that the flavoring agent is not limited to the substances listed above, and any flavoring agent conforming to FEMA codes or CAS codes is applicable.

In some embodiments, objects added to the composition do not include tobacco components.

In some embodiments, a method for manufacturing the aerosol-generating article includes one of paper-making process, dry paper-making process, slurry process and roller-formation process.

Implementation 6

Implementation 6 of this application provides an aerosol-generating article obtained from raw materials including the composition according to Implementation 1, an atomization agent, an adhesive and a plant fiber.

The aerosol-generating article is configured to be heated to generate a smokable aerosol.

In some embodiments, the arecoline has a mass percentage of 0.01-10%, preferably 0.2-10%, further preferably 1-10%, further preferably 1-5%, further preferably 1-4%, further preferably 1-3%, and further preferably 1-2%, based on total mass of the raw materials.

In some embodiments, the acid has a mass percentage of 0.01-10%, preferably 0.2-10%, further preferably 1-10%, further preferably 1-5%, further preferably 1-4%, further preferably 1-3%, and further preferably 1-2%, based on total mass of the raw materials.

In some embodiments, the atomization agent is selected from the group consisting of at least one of:

1,2-propanediol, 1,3-propanediol, glycerol, polyethylene glycol 200, polyethylene glycol 400, dipropylene glycol ether, ethanol, water, triethyl citrate, triacetin, caprylic capric triglyceride, isopropyl alcohol, sweet orange oil, lemon oil, peppermint oil, palm oil, peanut oil, corn oil or salad oil.

In some embodiments, the atomization agent has a mass percentage of 5-30%, preferably 10-30%, further preferably 10-25%, and further preferably 15-25%, based on total mass of the raw materials.

In some embodiments, the adhesive is selected from the group consisting of at least one of:

carboxymethyl cellulose, hydroxypropyl methyl cellulose, polyvinyl alcohol, rosin, xanthan gum, Arabic gum, guar gum, chitosan, pectin, locust bean gum, starch, sodium alginate or shellac.

In some embodiments, the adhesive has a mass percentage of 1-20%, preferably 1-15%, further preferably 1-10%, further preferably 3-10%, and further preferably 5-10%, based on total mass of the raw materials.

In some embodiments, the plant fiber is selected from the group consisting of at least one of:

areca nut fiber, wood pulp fiber, hemp pulp fiber, cotton pulp fiber, bagasse pulp fiber, bamboo pulp fiber or coconut pulp fiber.

In some embodiments, the plant fiber has a mass percentage of 40-80%, preferably 40-70%, further preferably 50-70%, further preferably 50-65%, and further preferably 50-60%, based on total mass of the raw materials.

In some embodiments, the raw materials further include a flavoring agent.

In some embodiments, the flavoring agent is selected from the group consisting of at least one of:

nerol, trans-2-hexenol, linalool, benzyl alcohol, 1-hexanol, leaf alcohol, alpha-terpineol, citronellol, beta-phenylethanol, linalool oxide, geraniol, isoamyl alcohol, octanol, hexanol, decanol, cinnamyl alcohol, heptanol, eugenol, maltol, ethyl maltol, thymol, isoeugenol, 2-methylbutyric acid, malic acid, n-valeric acid, n-hexanoic acid, edible acetic acid, n-caprylic acid, strawberry acid, butyric acid, citric acid, propionic acid, 3-methylvaleric acid, isovaleric acid, isoamyl acetate, amyl formate, geranyl formate, butyl formate, benzyl formate, formicacidhexenester, gamma-decanolactone, delta-nonalactone, gamma-octalactone, gamma-heptalactone, gamma-Undecalactone, delta-dodecalactone, benzaldehyde, strawberry aldehyde, cinnamaldehyde, furfural, citral, acetaldehyde, 3-methylthiopropanal, natural 3-mercapto-2-methylpentanal, isobutyraldehyde, trans-2-octenal, trans-2-nonenal, trans-2-decenal, trans,trans-2,4-heptadienal, 2,5-dimethylpyrazine, 2-acetylfuran, 2-ethyl-3 (5 or 6)-dimethylpyrazine, 2,3,5,6-tetramethylpyrazine, 2,3,5-trimethylpyrazine, 2-acetylpyrazine, acetophenone, beta-ionone, damascenone No. 2 (Firmenich), butanedione, alpha-ionone, acetoin (acetyl methyl carbinol), methyl heptenone, vanillin, ethyl vanillin, dihydrocoumarin, raspberry ketone, anisole, cedrol methyl ether, methyl-2-methyl-3-furyl disulfide, wintergreen oil, clove bud oil, 10-fold orange oil, Bois de rose oil, geranium oil, benzaldehyde, basil oil, ethyl vanillin, dihydrocoumarin, raspberry ketone, vanitrope, Tolu concrete, Peru concrete, oak extract, supercritical extract from espresso (water soluble), cocoa extract, coffee tincture, pandan leaf extract, vanilla extract, Labdanum concrete, orris oil or concrete, jasmine concrete, tree moss concrete (amber), tamarind extract, Zimbabwean tobacco extract, tobacco essence, burley tobacco extract, flue-cured tobacco absolute A, top note extract of flue-cured tobacco or top note extract of sun-cured tobacco.

It should be noted that the flavoring agent is not limited to the substances listed above, and any flavoring agent conforming to FEMA codes or CAS codes is applicable.

In some embodiments, the raw materials do not include tobacco components.

Embodiment 1

A heat-not-burn cigarette is prepared according to the following steps:

Step 1: preparation of a sheet substrate. Solid residues of an areca nut extract are selected and soaked in water at 60-80° C. for 0.5-2 h before filtering, the filtered solid is pulped to obtain a slurry, then 50-70 parts of slurry and 3-10 parts of solid adhesive are measured by weight and mixed well, and then a resulting mixed slurry is sent to a paper machine for molding and drying until the moisture content is about 10-15% to obtain a sheet substrate;

the solid adhesive may be one or more of carboxymethyl cellulose, hydroxypropyl methyl cellulose, polyvinyl alcohol, rosin, xanthan gum, Arabic gum, guar gum, chitosan, pectin, locust bean gum, starch, sodium alginate or shellac.

Step 2: preparation of a coating fluid. 1-50 parts of benzoic acid, 1-50 parts of arecoline, 2-20 parts of perfume and 40-80 parts of atomization agent are measured by weight, and mixed well to obtain a coating fluid;

the atomization agent is a mixture of glycerol and propylene glycol at a mixing ratio of 3-5:1.

Step 3: coating of the sheet substrate. The coating fluid obtained in the step 2 is weighed at 25-40% of the weight of the sheet substrate obtained in the step 1, then sprayed onto the sheet substrate, and allowed to stand under a constant temperature and a constant humidity for 40-60 h to obtain a plant sheet containing the composition.

Step 4: preparation of a heat-not-burn cigarette, the plant sheet obtained in the step 3 is made into a cigarette stick by size, and the cigarette stick is connected to a filter tip to obtain a heat-not-burn cigarette containing the composition.

The heat-not-burn cigarette prepared by the preparation method is compared with an ordinary heat-not-burn cigarette for smoking (an aerosol generation apparatus and a heating method therefor are not particularly limited, and resistance heating, electromagnetic heating, infrared radiation heating and so on can be used) and sensory quality evaluation: arecoline can be taken in from the heat-not-burn cigarette prepared by the preparation method, and the heat-not-burn cigarette can produce a similar effect of chewing areca nuts, with low irritation.

Implementation 7

Implementation 7 of this application provides an application of the composition according to Implementation 1 in preparing a liquid composition for a filter capsule; where the filter capsule includes a fragile shell and the liquid composition in the fragile shell.

In some embodiments, the arecoline has a mass percentage of 0.01-10%, preferably 0.2-10%, further preferably 1-10%, further preferably 1-5%, further preferably 1-4%, further preferably 1-3%, and further preferably 1-2%, based on total mass of the liquid composition.

In some embodiments, the acid has a mass percentage of 0.01-10%, preferably 0.2-10%, further preferably 1-10%, further preferably 1-5%, further preferably 1-4%, further preferably 1-3%, and further preferably 1-2%, based on total mass of the liquid composition.

In some embodiments, when the liquid composition is prepared, objects added to the composition include an atomization agent.

In some embodiments, the atomization agent is selected from the group consisting of at least one of:

1,2-propanediol, 1,3-propanediol, glycerol, polyethylene glycol 200, polyethylene glycol 400, dipropylene glycol ether, ethanol, water, triethyl citrate, triacetin, caprylic capric triglyceride, isopropyl alcohol, sweet orange oil, lemon oil, peppermint oil, palm oil, peanut oil, corn oil or salad oil.

In some embodiments, the atomization agent has a mass percentage of 5-30%, preferably 10-30%, further preferably 10-25%, and further preferably 15-25%, based on total mass of the liquid composition.

In some embodiments, objects added to the composition further include a flavoring agent.

In some embodiments, the flavoring agent is selected from the group consisting of at least one of:

nerol, trans-2-hexenol, linalool, benzyl alcohol, 1-hexanol, leaf alcohol, alpha-terpineol, citronellol, beta-phenylethanol, linalool oxide, geraniol, isoamyl alcohol, octanol, hexanol, decanol, cinnamyl alcohol, heptanol, eugenol, maltol, ethyl maltol, thymol, isoeugenol, 2-methylbutyric acid, malic acid, n-valeric acid, n-hexanoic acid, edible acetic acid, n-caprylic acid, strawberry acid, butyric acid, citric acid, propionic acid, 3-methylvaleric acid, isovaleric acid, isoamyl acetate, amyl formate, geranyl formate, butyl formate, benzyl formate, formicacidhexenester, gamma-decanolactone, delta-nonalactone, gamma-octalactone, gamma-heptalactone, gamma-Undecalactone, delta-dodecalactone, benzaldehyde, strawberry aldehyde, cinnamaldehyde, furfural, citral, acetaldehyde, 3-methylthiopropanal, natural 3-mercapto-2-methylpentanal, isobutyraldehyde, trans-2-octenal, trans-2-nonenal, trans-2-decenal, trans, trans-2,4-heptadienal, 2,5-diethylpyrazine, 2-acetylfuran, 2-ethyl-3 (5 or 6)-dimethylpyrazine, 2,3,5,6-tetramethylpyrazine, 2,3,5-trimethylpyrazine, 2-acetylpyrazine, acetophenone, beta-ionone, damascenone No. 2 (Firmenich), butanedione, alpha-ionone, acetoin (acetyl methyl carbinol), methyl heptenone, vanillin, ethyl vanillin, dihydrocoumarin, raspberry ketone, anisole, cedrol methyl ether, methyl-2-methyl-3-furyl disulfide, wintergreen oil, clove bud oil, 10-fold orange oil, Bois de rose oil, geranium oil, benzaldehyde, basil oil, ethyl vanillin, dihydrocoumarin, raspberry ketone, vanitrope, Tolu concrete, Peru concrete, oak extract, supercritical extract from espresso (water soluble), cocoa extract, coffee tincture, pandan leaf extract, vanilla extract, Labdanum concrete, orris oil or concrete, jasmine concrete, tree moss concrete (amber), tamarind extract, Zimbabwean tobacco extract, tobacco essence, burley tobacco extract, flue-cured tobacco absolute A, top note extract of flue-cured tobacco or top note extract of sun-cured tobacco.

It should be noted that the flavoring agent is not limited to the substances listed above, and any flavoring agent conforming to FEMA codes or CAS codes is applicable.

In some embodiments, objects added to the composition do not include nicotine and/or nicotine salts.

In some embodiments, the filter capsule is implanted in the aerosol-generating article.

In some embodiments, raw materials of the aerosol-generating article do not include tobacco components.

Implementation 8

Implementation 8 of this application provides a filter capsule including a fragile shell and a liquid composition in the fragile shell;

the liquid composition includes the composition according to Implementation 1 and an atomization agent.

In some embodiments, the arecoline has a mass percentage of 0.01-10%, preferably 0.2-10%, further preferably 1-10%, further preferably 1-5%, further preferably 1-4%, further preferably 1-3%, and further preferably 1-2%, based on total mass of the liquid composition.

In some embodiments, the acid has a mass percentage of 0.01-10%, preferably 0.2-10%, further preferably 1-10%, further preferably 1-5%, further preferably 1-4%, further preferably 1-3%, and further preferably 1-2%, based on total mass of the liquid composition.

In some embodiments, the atomization agent is selected from the group consisting of at least one of:

1,2-propanediol, 1,3-propanediol, glycerol, polyethylene glycol 200, polyethylene glycol 400, dipropylene glycol ether, ethanol, water, triethyl citrate, triacetin, caprylic capric triglyceride, isopropyl alcohol, sweet orange oil, lemon oil, peppermint oil, palm oil, peanut oil, corn oil or salad oil.

In some embodiments, the atomization agent has a mass percentage of 5-30%, preferably 10-30%, further preferably 10-25%, and further preferably 15-25%, based on total mass of the liquid composition.

In some embodiments, the liquid composition further includes a flavoring agent.

In some embodiments, the flavoring agent is selected from the group consisting of at least one of:

nerol, trans-2-hexenol, linalool, benzyl alcohol, 1-hexanol, leaf alcohol, alpha-terpineol, citronellol, beta-phenylethanol, linalool oxide, geraniol, isoamyl alcohol, octanol, hexanol, decanol, cinnamyl alcohol, heptanol, eugenol, maltol, ethyl maltol, thymol, isoeugenol, 2-methylbutyric acid, malic acid, n-valeric acid, n-hexanoic acid, edible acetic acid, n-caprylic acid, strawberry acid, butyric acid, citric acid, propionic acid, 3-methylvaleric acid, isovaleric acid, isoamyl acetate, amyl formate, geranyl formate, butyl formate, benzyl formate, formicacidhexenester, gamma-decanolactone, delta-nonalactone, gamma-octalactone, gamma-heptalactone, gamma-Undecalactone, delta-dodecalactone, benzaldehyde, strawberry aldehyde, cinnamaldehyde, furfural, citral, acetaldehyde, 3-methylthiopropanal, natural 3-mercapto-2-methylpentanal, isobutyraldehyde, trans-2-octenal, trans-2-nonenal, trans-2-decenal, trans,trans-2,4-heptadienal, 2,5-diethylpyrazine, 2-acetylfuran, 2-ethyl-3 (5 or 6)-dimethylpyrazine, 2,3,5,6-tetramethylpyrazine, 2,3,5-trimethylpyrazine, 2-acetylpyrazine, acetophenone, beta-ionone, damascenone No. 2 (Firmenich), butanedione, alpha-ionone, acetoin (acetyl methyl carbinol), methyl heptenone, vanillin, ethyl vanillin, dihydrocoumarin, raspberry ketone, anisole, cedrol methyl ether, methyl-2-methyl-3-furyl disulfide, wintergreen oil, clove bud oil, 10-fold orange oil, Bois de rose oil, geranium oil, benzaldehyde, basil oil, ethyl vanillin, dihydrocoumarin, raspberry ketone, vanitrope, Tolu concrete, Peru concrete, oak extract, supercritical extract from espresso (water soluble), cocoa extract, coffee tincture, pandan leaf extract, vanilla extract, Labdanum concrete, orris oil or concrete, jasmine concrete, tree moss concrete (amber), tamarind extract, Zimbabwean tobacco extract, tobacco essence, burley tobacco extract, flue-cured tobacco absolute A, top note extract of flue-cured tobacco or top note extract of sun-cured tobacco.

It should be noted that the flavoring agent is not limited to the substances listed above, and any flavoring agent conforming to FEMA codes or CAS codes is applicable.

In some embodiments, the liquid composition does not include nicotine and/or nicotine salts.

Implementation 9

Implementation 9 of this application provides an aerosol-generating article including the filter capsule according to Implementation 8.

In some embodiments, raw materials of the aerosol-generating article do not include tobacco components.

In the implementation, the aerosol-generating article can be prepared by a paper-making process, a dry paper-making process, a slurry process or a roller-formation process. Specifically, refer to the contents of the above implementations for raw materials and preparation steps of the aerosol-generating article.

A filter capsule can be implanted into a filter tip section (not limited to this position) of a heat-not-burn cigarette by embedding the filter capsule in a filter stick (not limited to this technology). When in use, a smoker can break the filter capsule to take in substances such as arecoline.

It should be noted that in the implementation, there is no special restriction on components and preparation processes of the fragile shell, as well as preparation processes of the filter capsule, and techniques well known to those skilled in the art can be used.

Embodiment 1

A liquid composition in a filter capsule is prepared according to the following formula:

5 wt % benzoic acid, 5 wt % arecoline, 80 wt % caprylic capric triglyceride and 10 wt % menthol.

Preparation method: benzoic acid and arecoline of the above formula weight are weighed, then caprylic capric triglyceride and menthol are added under stirring, and mixed well to obtain the liquid composition.

The heat-not-burn cigarette containing the filter capsule according to Embodiment 1 is compared with a heat-not-burn cigarette without a filter capsule for smoking and sensory quality evaluation: arecoline can be taken in from the heat-not-burn cigarette containing the filter capsule according to Embodiment 1, and the heat-not-burn cigarette containing the filter capsule according to Embodiment 1 can produce a similar effect of chewing areca nuts, with low irritation.

Implementation 10

Implementation 10 of this application provides an application of the composition according to Implementation 1 in manufacturing a chewing gum.

In some embodiments, when the chewing gum is manufactured, the arecoline has a mass percentage of 0.01-1%, preferably 0.01-0.8%, further preferably 0.01-0.6%, further preferably 0.01-0.5%, further preferably 0.05-0.5%, further preferably 0.1-0.5%, and further preferably 0.2-0.5%, based on total mass of raw materials of the chewing gum.

In some embodiments, when the chewing gum is manufactured, the acid has a mass percentage of 0.01-1%, preferably 0.01-0.8%, further preferably 0.01-0.6%, further preferably 0.01-0.5%, further preferably 0.05-0.5%, further preferably 0.1-0.5%, and further preferably 0.2-0.5%, based on total mass of raw materials of the chewing gum.

In some embodiments, when the chewing gum is manufactured, objects added to the composition include a gum base.

In some embodiments, when the chewing gum is manufactured, the gum base has a mass percentage of 20-75%, preferably 20-70%, further preferably 20-60%, further preferably 20-50%, further preferably 25-50%, further preferably 30-50%, further preferably 35-50%, and further preferably 35-45%, based on total mass of raw materials of the chewing gum.

In some embodiments, objects added to the composition further include a sweetening agent.

In some embodiments, the sweetening agent is selected from the group consisting of at least one of:

white granulated sugar, rock sugar, sucrose, maltose, corn syrup, glucose syrup, fructose, maltodextrin, polydextrose, xylitol, sorbitol, maltitol, erythritol, aspartame, acesulfame, sucralose, stevioside or neotame.

In some embodiments, when the chewing gum is manufactured, the sweetening agent has a mass percentage of 20-75%, preferably 20-70%, further preferably 20-60%, further preferably 20-50%, further preferably 25-50%, further preferably 25-40%, further preferably 25-35%, and further preferably 30-35%, based on total mass of raw materials of the chewing gum.

In some embodiments, objects added to the composition further include a filler material.

In some embodiments, the filler material is selected from the group consisting of at least one of:

sodium carbonate, sodium bicarbonate, potassium carbonate, calcium carbonate, dicalcium phosphate or sodium dihydrogen phosphate.

In some embodiments, when the chewing gum is manufactured, the filler material has a mass percentage of 0.03-23%, preferably 0.03-20%, further preferably 0.03-15%, further preferably 0.03-10%, further preferably 0.5-10%, further preferably 1-10%, further preferably 1.5-10%, further preferably 2-8%, and further preferably 2-6%, based on total mass of raw materials of the chewing gum.

In some embodiments, objects added to the composition further include a flavor.

In some embodiments, the flavor is selected from the group consisting of at least one of:

mint, spearmint, cinnamon, borneol or essence.

Implementation 11

Implementation 11 of this application provides a chewing gum obtained from raw materials including the composition according to Implementation 1 and a gum base.

In some embodiments, the arecoline has a mass percentage of 0.01-10%, preferably 0.2-10%, further preferably 1-10%, further preferably 1-5%, further preferably 1-4%, further preferably 1-3%, and further preferably 1-2%, based on total mass of the raw materials.

In some embodiments, the acid has a mass percentage of 0.01-10%, preferably 0.2-10%, further preferably 1-10%, further preferably 1-5%, further preferably 1-4%, further preferably 1-3%, and further preferably 1-2%, based on total mass of the raw materials.

In some embodiments, the gum base has a mass percentage of 20-75%, preferably 20-70%, further preferably 20-60%, further preferably 20-50%, further preferably 25-50%, further preferably 30-50%, further preferably 35-50%, and further preferably 35-45%, based on total mass of the raw materials.

In some embodiments, the raw materials further include a sweetening agent.

In some embodiments, the sweetening agent is selected from the group consisting of at least one of:

white granulated sugar, rock sugar, sucrose, maltose, corn syrup, glucose syrup, fructose, maltodextrin, polydextrose, xylitol, sorbitol, maltitol, erythritol, aspartame, acesulfame, sucralose, stevioside or neotame.

In some embodiments, the sweetening agent has a mass percentage of 20-75%, preferably 20-70%, further preferably 20-60%, further preferably 20-50%, further preferably 25-50%, further preferably 25-40%, further preferably 25-35%, and further preferably 30-35%, based on total mass of the raw materials.

In some embodiments, the raw materials further include a filler material.

In some embodiments, the filler material is selected from the group consisting of at least one of:

sodium carbonate, sodium bicarbonate, potassium carbonate, calcium carbonate, dicalcium phosphate or sodium dihydrogen phosphate.

In some embodiments, the filler material has a mass percentage of $0.0^3$-$2^3$%, preferably 0.03-20%, further preferably 0.03-15%, further preferably 0.03-10%, further preferably 0.5-10%, further preferably 1-10%, further preferably 1.5-10%, further preferably 2-8%, and further preferably 2-6%, based on total mass of the raw materials.

In some embodiments, the raw materials further include a flavor.

In some embodiments, the flavor is selected from the group consisting of at least one of:

mint, spearmint, cinnamon, borneol or essence.

Embodiment 1

A chewing gum is prepared according to the following formula:

54 wt % gum base, 23 wt % powdered sugar, 14 wt % glucose syrup, 4 wt % potassium carbonate, 3 wt % peppermint flavor, 1 wt % menthol, 0.5% benzoic acid and 0.5% arecoline.

Preparation method: a gum base is heated to 70-105° C. and stirred in a blender, then powdered sugar is added while allowing to cool to 60-80° C., then a buffer pair, additives, glucose syrup, benzoic acid and arecoline are added for finally rolling and molding to obtain a finished product.

Embodiment 2

A xylitol chewing gum is prepared according to the following formula:

54 wt % gum base, 23 wt % xylitol, 14 wt % non-sucrose, 4 wt % potassium carbonate, 3 wt % peppermint flavor, 1 wt % menthol, 0.5% benzoic acid and 0.5% arecoline.

Preparation method: a gum base is heated to 70-105° C. and stirred in a blender, then xylitol and non-sucrose are added while allowing to cool to 60-80° C., then a buffer pair, additives, benzoic acid and arecoline are added for finally rolling and molding to obtain a finished product.

The chewing gums prepared by the above preparation methods are compared with an ordinary chewing gum for edible and sensory quality evaluation: the chewing gums prepared by the above preparation methods can produce a similar effect of chewing areca nuts, with low irritation and good taste. Because the chewing gums do not contain lime powder and cellulose, the problems of abrasion and irritation of oral mucosa and induction of oral diseases when chewing areca nuts are avoided.

The written description discloses this application through embodiments, including the best mode, and also enables those skilled in the art to practice this application. The patentable scope of this application is defined by the claims, and may include other examples that occur to those skilled in the art. Such other examples are intended to be within the scope of the claims if they have structural elements that are not different from the literal language of the claims, or if they include equivalent structural elements without substantial differences from the literal language of the claims. All references cited herein are incorporated herein by reference to the extent that they do not cause inconsistency.

What is claimed is:

1. A composition configured to be edible or configured to be heated to generate an aerosol for inhaling, comprising benzoic acid and arecoline, wherein a mass ratio of the benzoic acid to the arecoline is equal to or less than 1, a pH value of the composition is between 6.1 and 6.7.

2. The composition according to claim 1, wherein the composition further comprises an acid selected from the group consisting of at least one of:

formic acid, acetic acid, propionic acid, butyric acid, isovaleric acid, 2-methylbutyric acid, valeric acid, 3-methylvaleric acid, 2-methyl-2-pentenoic acid, trans-2-hexenoic acid, hexanoic acid, heptanoic acid, octanoic acid, 2-nonenoic acid, decanoic acid, dodecanoic acid, tetradecanoic acid, hexadecanoic acid, octadecanoic acid, arachidic acid, salicylic acid, oxalic acid, citric acid, sorbic acid, tartaric acid, adipic acid, hydrochloric acid, hydrobromic acid, glycine, alanine, valine, leucine, isoleucine, methionine, phenylalanine, proline, tryptophan, serine, tyrosine, cysteine, methionine, asparagine, glutamine, threonine, aspartic acid, glutamic acid, lysine, arginine or histidine.

3. The composition according to claim 2, wherein the arecoline and the benzoic acid form an arecoline salt.

4. The composition according to claim 1, wherein the arecoline and the benzoic acid form an arecoline salt.

5. A product with an *areca* nut flavor, wherein the product comprises the composition according to claim 1.

6. The product according to claim 5, wherein the product is an aerosol generation substrate configured to be atomized to generate the aerosol.

7. The product according to claim 6, wherein the aerosol generation substrate is a liquid phase configured to be atomized by any one of a heating atomizer, an ultrasonic atomizer, an air compression atomizer or a press-type spraying apparatus to generate an aerosol.

8. The product according to claim 6, wherein the aerosol generation substrate is a solid phase configured to generate a smokable aerosol when heated below an ignition point.

9. The product according to claim 5, wherein the product is a filter capsule used in an aerosol-generating article.

10. The product according to claim 5, wherein the product is a chewing gum.

11. The product according to claim 5, wherein the product further comprises a flavoring agent.

12. The product according to claim 11, wherein the flavoring agent is selected from the group consisting of at least one of nerol, trans-2-hexenol, linalool, benzyl alcohol, 1-hexanol, leaf alcohol, alpha-terpineol, citronellol, beta-phenylethanol, linalool oxide, geraniol, isoamyl alcohol, octanol, hexanol, decanol, cinnamyl alcohol, heptanol, eugenol, maltol, ethyl maltol, thymol, isoeugenol, 2-methylbutyric acid, malic acid, n-valeric acid, n-hexanoic acid, edible acetic acid, n-caprylic acid, strawberry acid, butyric acid, citric acid, propionic acid, 3-methylvaleric acid, isovaleric acid, isoamyl acetate, amyl formate, geranyl formate, butyl formate, benzyl formate, formicacidhexenester, gamma-decanolactone, delta-nonalactone, gamma-octalactone, gamma-heptalactone, gamma-Undecalactone, delta-dodeca-lactone, benzaldehyde, strawberry aldehyde, cinnamalde-hyde, furfural, citral, acetaldehyde, 3-methylthiopropanal, natural 3-mercapto-2-methylpentanal, isobutyraldehyde, trans-2-octenal, trans-2-nonenal, trans-2-decenal, trans, trans-2,4-heptadienal, 2,5-dimethylpyrazine, 2-acetylfuran, 2-ethyl-3 (5 or 6)-dimethylpyrazine, 2,3,5,6-tetrameth-ylpyrazine, 2,3,5-trimethylpyrazine, 2-acetylpyrazine, acetophenone, beta-ionone, damascenone No. 2 (Firmen-ich), butanedione, alpha-ionone, acetoin (acetyl methyl car-binol), acetoin (acetyl methyl carbinol), methyl heptenone, vanillin, ethyl vanillin, dihydrocoumarin, raspberry ketone, anisole, cedrol methyl ether, methyl-2-methyl-3-furyl disul-fide, wintergreen oil, clove bud oil, 10-fold orange oil, Bois de rose oil, geranium oil, benzaldehyde, basil oil, ethyl vanillin, dihydrocoumarin, raspberry ketone, vanitrope, Tolu concrete, Peru concrete, oak extract, supercritical extract from espresso (water soluble), cocoa extract, coffee tincture, pandan leaf extract, vanilla extract, Labdanum concrete, orris oil or concrete, jasmine concrete, tree moss concrete (amber), tamarind extract, Zimbabwean tobacco extract, tobacco essence, burley tobacco extract, flue-cured tobacco absolute A, top note extract of flue-cured tobacco or top note extract of sun-cured tobacco.

\* \* \* \* \*